(12) United States Patent
Hata (10) Patent No.: US 8,569,018 B2
(45) Date of Patent: Oct. 29, 2013

(54) SIMPLIFIED METHOD FOR DIGESTION OF CELLULOSIC BIOMASS

(75) Inventor: Seiji Hata, Tokyo (JP)

(73) Assignee: Biomass Conversions, LLC, Palos Verdes Estates, CA (US)

( * ) Notice: Subject to any disclaimer, the term of this patent is extended or adjusted under 35 U.S.C. 154(b) by 410 days.

(21) Appl. No.: 12/933,865

(22) PCT Filed: Mar. 31, 2009

(86) PCT No.: PCT/US2009/038993
§ 371 (c)(1),
(2), (4) Date: Sep. 21, 2010

(87) PCT Pub. No.: WO2009/124072
PCT Pub. Date: Oct. 8, 2009

(65) Prior Publication Data
US 2011/0020874 A1  Jan. 27, 2011

Related U.S. Application Data

(60) Provisional application No. 61/041,379, filed on Apr. 1, 2008.

(51) Int. Cl.
*C12P 19/00* (2006.01)

(52) U.S. Cl.
USPC .............................. 435/72; 435/161; 435/183

(58) Field of Classification Search
None
See application file for complete search history.

(56) References Cited

U.S. PATENT DOCUMENTS

2003/0225206 A1   12/2003   Lee et al.

FOREIGN PATENT DOCUMENTS

WO   WO 02/057317 A   7/2002
WO   WO 2007/084711    7/2007

OTHER PUBLICATIONS

Chung et al., Surfactant-free thermochromic hydrogel system:PVA/BOrax gel networks containing pH-sensitive dyes, Journal of Applied Polymer Science, vol. 91, p. 890-893, 2004.*
Hennink et al., Novel crosslinking methods to design hydrgels, Advanced Drug Delivery Reviews, vol. 54, p. 13-36, 2002.*
HOffman, Hydrogels for biomedical applications, Advanced drug Delivery Review, vol. 54, p. 3-12, 2002.*
JP2000-080126 Machine translation.*
Database WPI Week 200003, Thomson Scientific, London, GB; AN 2000-033622 JP 11 302448 A (Asahi Kasei KK) Nov. 2, 1999 Abstract.
Mosier N. et al., "Features of promising technologies for pretreatment . . . ," Bioresource Technology, Elsevier, GB, vol. 96, No. 6, Apr. 1, 2005, pp. 673-686.
International Search Report for PCT/US2009/038993, mailed Sep. 17, 2009.

\* cited by examiner

*Primary Examiner* — Jon P Weber
*Assistant Examiner* — Tiffany Gough
(74) *Attorney, Agent, or Firm* — Venable LLP; Stefan J. Kirchanski (57) ABSTRACT

The inventive process converts cellulosic biomass into a gel-like state that is readily hydrolyzed by appropriate enzymes. First the biomass is mechanically reduced in size. The biomass is then mixed and kneaded with an aqueous solution of a hydrophilic polymer that acts as a conditioning agent or as a co-solvent. During mixing the cellulose (and hemicellulose) in the biomass swells and becomes hydrated forming a viscous gel-like material. The processed material can then be thinned through the addition of water whereupon hydrolytic enzymes are mixed into the material and rapid hydrolysis into free sugars takes place. Dextrins are effective hydrophilic polymers for conditioning biomass. Polyvinyl alcohol is a particularly effective conditioning agent for use with biomass when converted into a viscous gel by adding borate ions.

9 Claims, 6 Drawing Sheets

SIMPLIFIED METHOD FOR DIGESTION OF CELLULOSIC BIOMASS

CROSS-REFERENCE TO PRIOR APPLICATIONS

The present application is a U.S. National Phase application of and claims priority from PCT/US2009/038993, filed on Mar. 31, 2009 designating the United States, which in turn was based on and claims priority from U.S. Provisional Patent Application Nos. 61/041,379 filed Apr. 1, 2008 all of which applications are incorporated herein by reference.

U.S. GOVERNMENT SUPPORT

Not Applicable.

BACKGROUND OF THE INVENTION

For the last several decades there have been repeated warnings concerning energy shortages. The general pattern has been for energy prices to spike sharply resulting in a significant economic downturn which temporarily takes the pressures off of energy supplies. At the same time half-hearted energy conservation measures are established. In the past this resulted in a temporary drop in energy prices so that rampant energy consumption soon resumed and energy conservation and long-term energy planning were completely forgotten. At this time the rapid development of China and India are placing increasing pressure on energy supplies. This demand seems likely to cushion the typical cyclic drop in prices. Recently the price of oil spiked to $150.00 per barrel or more, and it seems as if prices may eventually return to those levels if energy conservation is not improved and new energy sources are not found.

Furthermore, energy supplies are finite. Best estimates are that oils supplies will be mostly depleted within forty or so years. Even with the discovery of new oil fields and improved recovery from existing fields, this estimate is highly unlikely to be increased even two-fold to eighty years. Thus, baring drastic improvements in efficiency or tremendous conservation efforts, some individuals who are now alive will almost certainly see the end of a petroleum powered world just as our ancestors not that many generation back saw the end of a horse powered technology. Some have pinned their hopes on nuclear power. Unfortunately, the supply of nuclear fuel is also limited particularly considering the inefficient nuclear reactors now in use. Furthermore, the nuclear waste problem is so critical that our civilization could probably not safely depend on nuclear energy even if the fuel supply were unlimited.

The picture for other popular fossil fuels is not much brighter than that for oil. It is estimated that current natural gas supplies will be exhausted in about sixty years. Even if the estimated time is doubled, it would appear that wide spread dependence on natural gas will end in no more than one hundred and twenty years. Coal is perhaps the most abundant fossil fuel; there is thought to be at least a 200 year supply. That means that unless alternative energy technologies are soon developed our civilization will become entirely dependant on coal within the next fifty to one hundred years. Yet coal is the fossil fuel that was developed earliest and was largely supplanted by oil and natural gas because coal combustion is dirty and leaves large volumes of ash. Not to mention the terrible environmental costs of coal mining.

However, it is probably not a shortage of coal that will necessitate an abandonment of coal use. Rather it will be the environmental consequences of continued release of fossil carbon dioxide into the atmosphere. This problem, often called global warming, results from combustion of any fossil fuel. It is just that oil will probably be exhausted before the full brunt of the problem is felt. Global warming is probably not a good term because while overall global temperatures are increasing due to excess atmospheric carbon dioxide, the real problem is not warming per se but rather is drastic climate change. The Earth's climate is always changing—at some times more rapidly that at other times. For example, during the relatively recent past drastic climate change that took place at the end of the ice age; this climate change although rapid by geological standards was sufficiently slow that living organisms could either adjust to the new climate or relocate to an area with a more amenable climate. Thus as the glaciers retreated and temperatures warmed "arctic" species adapted to cold temperatures moved north or into higher elevations. There is every indication that the climate changes resulting from burning of fossil fuels will be too rapid to allow living organisms to relocate. The result will be extreme loss of species and overall biological diversity with a species extinction rate much higher than the already high extinction rate caused by the spread of our civilization.

Until some entirely new energy source such as fusion is perfected, the best answer to the energy conundrum would appear to be greatly increased conservation coupled with exclusive use of renewable energy sources. Most energy on our planet comes ultimately from the sun. Therefore, solar energy in the form of photovoltaic electricity and solar heating are ideal. However, direct solar energy cannot satisfy all of our needs. Hydroelectric power and wind generated power are two other forms of renewable solar-based energy. None of these power sources result in changes in atmospheric carbon dioxide. Biomass energy (i.e., wood and other plant materials) may be the ideal complement to solar energy. This may seem surprising because biomass energy is normally obtained through combustion of the biomass, and such combustion releases carbon dioxide into the atmosphere. However, biomass is renewable. If plantations of green plants are grown to produce biomass, the released carbon dioxide will quickly be sequestered in new plant material. Thus, the carbon dioxide is used over and over, and the total level of atmospheric carbon dioxide does not continue to increase, as with the burning of fossil fuels. The real problem is how to integrate biomass energy into our economy. There is presently a marked shortage of wood burning stream trains and wood burning automobiles. Nor is direct combustion of biomass in power plants particularly viable because our electrical generation systems are adapted to use liquid oil or natural gas or even pulverized coal.

There has been considerable effort to produce liquid fuel (primarily ethanol) from biomass. This involves fermentation of sugars derived directly from plant products like corn or indirectly from the digestion of cellulosic biomass into fermentable sugars. The technology for fermenting directly derived sugars is well established. Presently, the United States is increasingly moving towards a fuel system based on ethanol derived from corn. While this approach may be politically favored by corn raising areas, it contains a potentially fatal flaw. Diversion of corn from food uses may result in a dramatic increase in food prices. Even more of a problem is the considerable requirement of nitrogen fertilizer for efficient cultivation of corn. The primary source of nitrogen fertilizer is an energy intensive industrial process that consumes almost as much energy as is captured in corn derived ethanol. This is particularly true because only a fraction of the energy in the corn plant is captured by converting corn grain into ethanol. A great deal of energy remains in the cellulosic biomass of the plant and is not reclaimed as ethanol.

Probably, the greatest potential source of renewable energy is in cellulosic biomass. The conversion of cellulose into fermentable sugar is difficult and at the present not terribly efficient. Typically enzymes or acids are used to hydrolyze the cellulosic biomass into fermentable sugars. Adequate mechanical pretreatment of the biomass is essential. In some processes the biomass is chemically pretreated and then "exploded" by rapid changes in temperature and pressure. Such processes may create large amounts of hazardous chemical waste. Other processes cook wood chips in acid in devices rather like those used to produce wood pulp for paper manufacturing. To date none of these approaches has proven to be highly successful. The present inventor has earlier tried to solve the problems of the present technology by reducing biomass into sufficiently small particles. The inventor found that such particles (called cellulosic micropowder) can be readily hydrolyzed into sugars and other organic monomers either by means of enzymes or by means of chemical hydrolysis. Probably because of the very small size of the particle, hydrolytic enzymes are far more effective than they are on cellulosic biomass prepared in other ways. The main drawback of this approach appears to be the complexity of the devices used to make the micropowder and the energy consumed by them. Therefore, the inventor has attempted to develop an even more efficient method to convert cellulosic biomass into fermentable sugars.

SUMMARY OF THE INVENTION

The inventive process converts cellulosic biomass into a gel-like state that is readily hydrolyzed by appropriate enzymes. The inventor refers to this process as "conditioning" or "co-solvation." First the biomass is mechanically reduced in size. Depending on the precise characteristics of the biomass source the process can be useful on material where the maximum dimension is less than about 2 mm. However, optimum results are achieved with biomass particles with a maximum dimension of less than 100 micrometers—preferably in the 20-70 micrometer size range. Of course, biomass powder having even smaller dimensions works perfectly, but the improvement, if any, from using material having such smaller dimensions does not seem to justify the additional effort in further reducing the size of the biomass particles. The biomass is then mixed/kneaded with an aqueous solution of a hydrophilic polymer that acts as a conditioning agent or as a co-solvent. The resulting mixture is mixed and kneaded and the cellulose (and hemicellulose) in the biomass swells and becomes hydrated. This results in a viscous gel-like material. The processed material can then be thinned through the addition of water whereupon hydrolytic enzymes are mixed into the material. The viscosity of the mixture rapidly decreases as the polysaccharides are broken down into free sugars. If the biomass has been completely conditioned, hydrolysis into free sugars occurs within a few hours or less.

Dextrins are effective hydrophilic polymers for conditioning biomass. Experimentation has shown that the initial conditioning liquid should have significant viscosity or else the conditioning process is extremely slow. The inventor believes that a viscous liquid effects the transmission of the mixing/kneading energy to the biomass particle. This transmitted energy is involved in hydrating the biomass and causing the cellular structure of the biomass particles to break down. With the dextrins, the mixing/kneading is most effective at an elevated temperature (e.g., 70-90° C.). Part of this is due to the elevated temperature maintaining the mixture flexible. As the biomass absorbs water, the mass becomes thicker and thicker. If the thick mass is allowed to cool, it may harden completely. With the dextrins is beneficial to periodically add small aliquots of water to keep the mass from becoming too thick. Excessive additions of water should be avoided because if the viscosity is reduced too much, the rate of the conditioning process slows dramatically. The best practice with the dextrin conditioning agents is to alternate water and biomass additions to maintain optimum processing conditions. The process is effective with mixtures that are about 30% to 50% by weight biomass. Generally, the complete process requires 5-10 hours of mixing/kneading.

Polyvinyl alcohol (PVA) is another effective conditioning agent for use with biomass. It appears that PVA can be more effective than dextrins and similar polysaccharides perhaps because it is possible to convert a PVA solution into a viscous gel by adding agents such as borate that crosslink the PVA. When biomass particles are mixed/kneaded into such a PVA gel, the conditioning process progresses rapidly at room temperature. Unlike the dextrin conditioned material, the PVA conditioned material maintains its flexibility allowing the use of a rolling and stacking manipulation which enhances processing. As with dextrin conditioning water can be added as needed to control the viscosity of the mixture; however, water additions are generally not necessary. Like the dextrin conditioning the PVA process can handle mixtures that are about 30%-50% by weight biomass. The PVA processing is generally faster than the dextrin process and can reach completion in as little as one to two hours. Following conditioning, the thick gel is thinned by the addition of water after which hydrolytic enzymes are mixed in. The viscosity of the mixture is rapidly reduced by enzymatic hydrolysis which is largely complete in less than five hours.

The key to the process is mixing the biomass particles in the presence of a viscous hydrophilic polymer solution. Other hydrophilic polymers capable of making viscous solutions are expected to be effective including crosslinked polyacrylic acid (and copolymers) and polysaccharides such as pectin, locust bean gum, guar gum, konjac gum and alginate that can be crosslinked by either borate ions, calcium ions or other divalent cations. The choice of condition agent depends, to some extent, upon the economics of the availability of the material and the problems, if any, in the disposal of the spent material. In the case of dextrins they can be readily hydrolyzed by a amylase and fermented by yeast. In the case of PVA, the material can be recovered from the hydrolysis liquid and recycled.

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide improved methods for reducing biomass into a readily hydrolyzable form through the use of chemical conditioning/solvation with hydrophilic polymers.

The present inventor has analyzed the processes used to reduce starch to fermentable sugars. In a factory that converts corn into ethanol the corn starch (primarily a glucose α1-4 polymer) is first hydrated by "cooking" it in water. In the presence of water at an elevated temperature the starch polymers become hydrated and form a gel. The starch polymers are generally too long to become fully soluble; however, as a hydrated gel the polymers are readily accessible to enzymatic attack. Enzymes such as a amylase cleave the α1-4 bonds and reduce the starch gel into a liquid solution of shorter polymers containing α1-6 branches and simple sugar (glucose). Addition of gluco-amylase cleaves the α1-6 bonds and completes the conversion of the starch into fermentable sugar (glucose).

If it were possible to hydrate cellulosic biomass in a manner similar to starch, it should be possible to convert the hydrated cellulose to simple sugars much more efficiently. Industry has a great deal of experience with treatment of cellulose, and it is generally know that hydration of cellulose into a semi-soluble gel is not readily possible. If cellulosic biomass (such as wood chips) is cooked and agitated at elevated temperatures in the presence of certain chemicals, it is possible to separate the lignin from the cellulose to yield relatively pure (but still insoluble) cellulose. This is essentially the process used to convert wood chips into paper pulp. It is also know that certain alkaline compositions and organic solvents such as carbon disulfide can be used to actually dissolve cellulose. More recently more benign ionic liquids (such as 1-butyl-3-methylimidazolium chloride) have been discovered to dissolve cellulose. While any of these approaches are useful in regenerating cellulose for textile or material uses (e.g., cellophane), these compounds are toxic and/or expensive and are generally not compatible with enzymes for further reduction of the dissolved cellulose into simple sugars.

Therefore, the inventor searched for a simpler and safer way to hydrate cellulose. It seemed likely that the well-known paracrystalline regions of cellulose found in cellulosic biomass were at least partly responsible for the resistance of cellulose to hydration. In his earlier experiments with wet (see WO/2002/057317) and dry (see WO/2007/106773) disruption of cellulosic biomass had shown that it was possible to disrupt at least some paracrystalline cellulose through repeated application of water (the wet process) or even directly through mechanical force (the dry process). The inventor developed the theory that strenuous mixing or kneading of cellulose in the presence of an aqueous solution of hydrophilic polymers could combine the effects of his wet and dry processes. A hydrophilic polymer would increase the viscosity of water thereby allowing more efficient transfer of mechanical energy from mixing. Also, the presence of the polymer alters the dielectric constant of the surrounding medium which can have an effect on hydrogen bond strength. This is particularly true because the hydrophilic polymer molecules would interact with the surface cellulose molecules and help "peel" them away from the insoluble mass of cellulose. At the same time the hydrophilic polymers would intercalate between the cellulose polymer chains, disrupting paracrystalline regions and maintain the cellulose in a hydrated semi-soluble form. Essentially, the hydrophilic polymer would act as a "co-solvent" or "conditioner" for cellulose. It should be appreciated that while the term "co-solvent" is used for convenience, the hydrophilic polymers so not act as true solvents in the sense that they bring the cellulose completely into solution. Rather, the polymers condition the cellulose and convert it into a gel-like form that is amenable to rapid enzymatic hydrolysis. As demonstrated below, hydrophilic polymers do act as co-solvents for cellulose in that they greatly simplify the task of converting biomass into a form of cellulose that can be readily hydrolyzed by enzymes.

Figure 1:
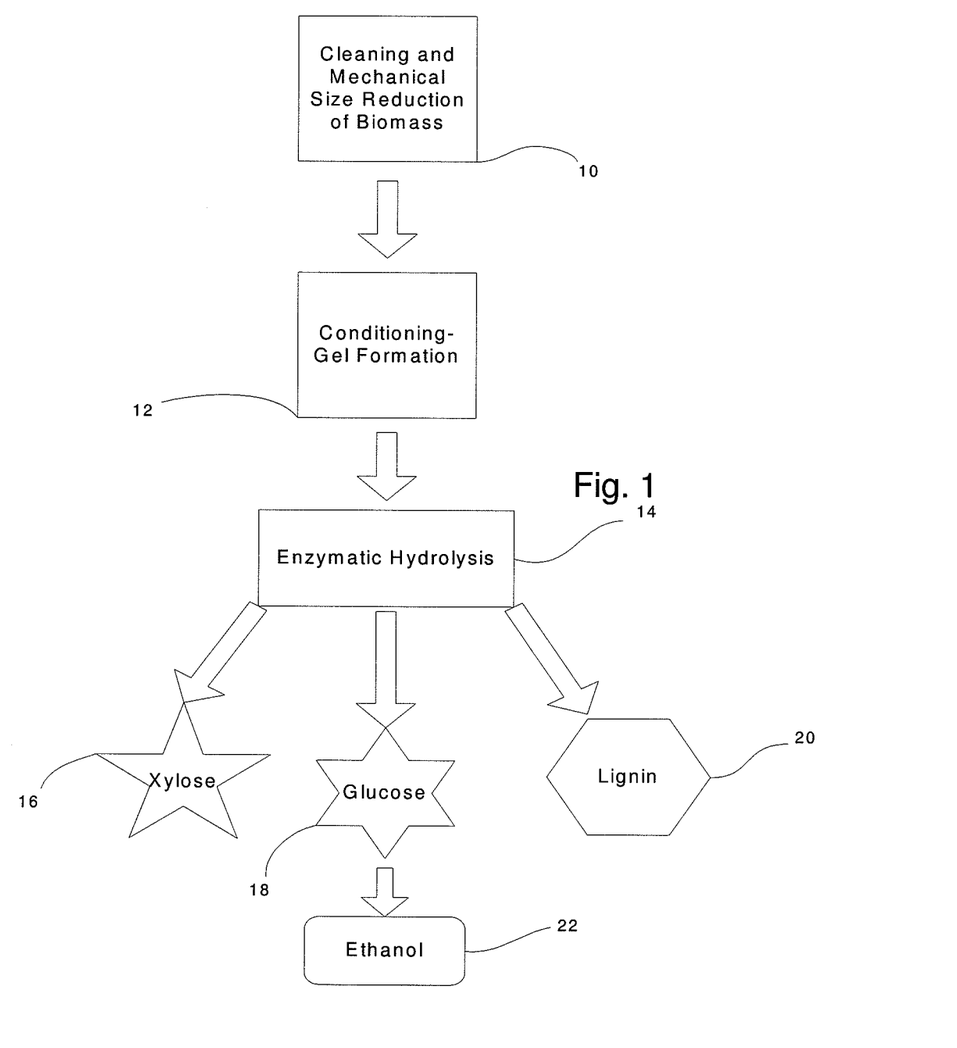
FIG. 1 is a diagram of the overall steps in practicing the inventive conditioning process.

The overall outline of the process is shown in FIG. 1. In a first step 10 the biomass is reduced in size to facilitate the following steps of the process. Preparing biomass is relatively simple; dirt, rocks, bark and other non-cellulosic components are removed as much as practicable. The resulting "cleaned" biomass or feedstock which is primarily cellulose is then reduced by cutting or similar manipulations so that the largest dimension is approximately 2 mm or less. The cutting machines described in the inventor's earlier patent applications are ideal for this task. Saw dust or other mass that has dimensions substantially smaller than 2 mm will process more rapidly. While it is not essential to reduce dimensions substantially below 2 mm, it will be appreciated that there is a tradeoff between time/energy spent in the kneading/mixing step and the time/energy spent in reducing the dimensions of the biomass. The mechanisms described in the inventor's earlier applications (above) are ideal although other suitable apparatus will be apparent to one of skill in the art. A preferred size of the biomass is less than 2 mm diameter; a more preferred size is less than 1 mm in diameter; and a most preferred size range is particles having a diameter of about 20-70 micrometers—that is less than 100 micrometers. Plant cells are generally less than 100 micrometers in diameter, and a large number of plant cells are in the 20-70 micrometer range. Thus, it is relatively easy to reduce biomass to particles in this range. It will be appreciated that the crude biomass is not entirely cellulose glucose polymer. It also contains a variable amount of hemicellulose (polysaccharides containing sugars such as xylose, mannose, galactose, rhamnose, glucose and arabinose as well as mannuronic and galacturonic acid). The predominant sugar in hemicellulose is the pentose sugar xylose. Most biomass also contains lignin which is a complex hydrophobic polymer of derivatives of coniferyl alcohol, p-coumaryl alcohol and sinapyl alcohol (known as lignols). Lignin is believed to cement the cellulosic and hemicellulosic structures together.

In a second step 12 the biomass particles are mixed into a gel reaction conditioning agent. The biomass is mixed or kneaded with the conditioning agent during which time the cellular structure of the biomass is broken down. The cellulose and hemicellulose are partially hydrated and the interaction between these polysaccharides and lignin is disrupted so that the microscopic structures of the plant cell wall are broken down. The resulting product is quite viscous so that the viscosity must be reduced by the addition of water. At step 14 hydrolytic enzymes are mixed in, and the conditioned biomass rapidly becomes less viscous. Following enzymatic hydrolysis glucose 18 and xylose 16 (and the other hemicellulose monomers) are in solution. Lignin 20 is present as small particles but the chemical structure of the partly disrupted lignin has yet not been characterized. The lignin can be removed by filtration or centrifugation. The soluble sugars can be purified by methods well known in the art (e.g., chromatographic methods) if the xylose (a valuable natural product) is to be reclaimed. The sugar solution (either before or after separation) is then be subjected to alcoholic fermentation with yeast to produce ethanol as is also well known in the art.

The process was first developed employing oligo-saccharides as a biomass conditioner. In addition other hydrophilic polymers which act as viscosity increasing co-solvents have proven even more effective; all these materials are inexpensive and generally non-toxic. The presently preferred oligo-saccharides are dextrins (relatively short α1-4 glucose polymers), maltodextrins and even maltose. As polymer length increases, viscosity of an aqueous solution of the dextrin polymer increases. It appears that the effectiveness is related to the amount of oligo-saccharide needed to achieve sufficient viscosity. In the case of very short polymers, like maltose, a very concentrated solution is used for optimal results. Polyvinyl alcohol is the presently preferred non-carbohydrate hydrophilic polymer.

The process using oligo-saccharides takes prepared biomass, adds the dextrin "co-solvent" solution and then mixes the resulting mass at elevated temperature (about 60° C. to 90° C.) until a viscous translucent or even transparent gel-like mixture results. During the mixing the biomass goes through a swelling-hydration step. Finally, the cellulose is more or less completely "dissolved" into a viscous gel. With dextrins heating is generally necessary to maintain the flexibility of the biomass mixture.

In one experiment, a 10-20% by weight mixture of size reduced biomass was stirred in a dextrin co-solvent and then "kneaded" (mixed) at the elevated temperature (about 60° C. to 90° C.) until a viscous gel was formed. By "knead" is meant a solid and liquid mixing procedure not unlike that applied to flour and water in the formation of bread dough. Commercial mixing apparatus similar to those suitable for production of flour-based dough can be used so long as there is a way to maintain the elevated temperature. The inventor has found that dual screw mixers/extruders traditionally used in the preparation of plastic resins for coating or injection molding are particularly suitable. Normally, approximately one hour mixing is needed to hydrate the cellulosic biomass and transform it into an extremely viscous translucent or transparent gel. If purified cellulose such as filter paper is used as a test starting material the resulting gel is colorless and transparent. Usually a number of air bubbles are trapped in the gel preventing it from being water clear. Also, plant pigments and insoluble material reduce the clarity of the gel. The weight of solids in the mixture can reach 50% and higher.

Normally biomass will contain lignin and hemicellulose as well as cellulose. If, for example, bagasse (the pulp left over from the extraction of sugar from crushed sugar cane) is mixed with the dextrin co-solvent and kneaded for about one hour at an elevated temperature, the resulting gel has a yellowish or brownish tint and is less transparent than a gel made from purified cellulose. Microscopic inspection of the gel reveals that most of the cellular structures have been largely disrupted. However, the epidermal cells of sugar cane are somewhat silicified and part of this cellular structure survives the kneading process. In addition, small traces of heavily lignified vascular elements may also remain although longer processing will cause them to fully disintegrate.

Experiments with a variety of plant materials have demonstrated that some materials are more resistant to co-solvation than others. It has been discovered that significantly faster results can be achieved by starting with biomass powders wherein the particle size is in the range of 20-70 micrometers in diameter—that is less than 100 micrometers. A variety of mechanical processing devices can readily reduce cellulosic biomass to particles in this size range without undue processing. The devices used in the inventor's earlier patent applications are suitable. As disclosed in those patents, it is more difficult to reduce the biomass to a micrometer or sub-micrometer size range. The advantage of the current process is that it takes over and optimally processes biomass particles that can be readily produced by the usual mechanical devices.

Kneading biomass with the dextrin co-solvent, particularly at an elevated temperature, results conversion of solid cellulose into an extremely viscous gel or dough, not entirely unlike the conversion of starch into a gel upon cooking—at least in appearance. It has been determined that mixtures having higher levels of biomass can be more effectively solvated; it appears that solvation occurs most readily in a viscous solution. The elevated temperature is necessary to maintain the flexibility of such viscous mixtures, and if they are allowed to cool, they tend to solidify. The inventor believes that the higher level of viscosity during kneading caused by added biomass increases the rate of solvation. The next step of the process is analogous to the starch process—namely liquefaction of the gel. In most cases the kneaded biomass will be so viscous or dough-like that it is necessary to add water to reduce the viscosity prior to enzyme addition.

With cellulose gel, liquefaction is achieved by addition of liquefaction enzymes (endo-cellulases and endo-glucanases) to the gel with continued mixing. Following liquefaction of the gel, saccharification enzymes (exo-cellulases, cellobio-glucanases and mixed β-glucanases) are added to reduce the remaining cellulose to free glucose. It is also possible to add both types of enzymes simultaneously so that liquefaction and saccharification proceed at the same time. The favored enzymes are those produced by *Trichoderma reesii* and *viride* as well as species of *Aspergillus, Acremonium* and *Penicillium*. Enzymes (for example, Meicellase, a mixture of *T. viride* enzymes containing cellulases, xylanase, β-glucosidase and α-L-arabinosidae) from Meiji Seika Co. Ltd. of Tokyo, Japan were used in several experiments although appropriate enzymes from other organisms and commercial sources can serve as well. It is important to appreciate that the present process converts the cellulose into a form that is more readily hydrolyzed by essentially any enzyme having the appropriate specificity. Generally, the weight of the added enzyme is about $\frac{1}{100}$ of the weight of the cellulosic feedstock. Depending on the precise enzyme used the optimum reaction takes place between about 45° C. and 60° C. It will be apparent to one of ordinary skill in the art that there is considerable overlap in types of enzymatic activity between the liquefaction and saccharification enzymes; therefore, the liquefaction enzymes release a significant amount of free sugar.

A typical experiment will now be described in detail. A starting solution or syrup of dextrin in water was produced by adding 50 g of dextrin (e.g., maltose) to 12.5 g of water (an 80% by weight solution). Dextrins with higher DE (dextrose equivalents) ratings produce solutions with greater viscosity and are effective at a lower weight percentage. This shows that viscosity of the co-solvent is important with more viscous solvents being markedly more effective. Of course, viscous co-solvents may have the disadvantage of rendering the biomass/co-solvent mixture too viscous for ready mixing or kneading. Typically, the pH of the swelling and hydration step is near neutrality. In this experiment the weight ratio between cellulose and dextrin was at least 5:2. Initially, 10 g of cellulose (in the form of filter paper cut into 1 cm squares) was added to the dextrin solution and the resulting mixture was mixed-kneaded at 80° C. for around one hour. The cellulose became swelled by this process forming a transparent gel or "dough". If the gel is cooled to room temperature at this point, the viscosity increases significantly. At least an additional 10 g of cellulose (20% by weight cellulose mixture) were then added and absorbed into the gel over a similar period of time. During further processing a relatively small amount of water (here 5 ml) was added slowly to decrease temporarily the viscosity and improve the ease of processing. The decreased viscosity allows more vigorous mixing including "beating" in which the solution encounters shear stresses to help break down fibrils and other plant cell wall structures. As more and more of the cellulose became swelled and hydrated, the viscosity increased and an additional aliquot of water (here 10 ml) was added thereby again significantly decreasing the viscosity. At this point another aliquot of cellulose was added and this addition loop (see FIG. 1) was repeated between 5 and 10 times. As the amount of cellulose increased, the processing time for each iteration decreased slightly. When the addition process was repeated five times the final solution was about 30% cellulose by weight.

Figure 2:
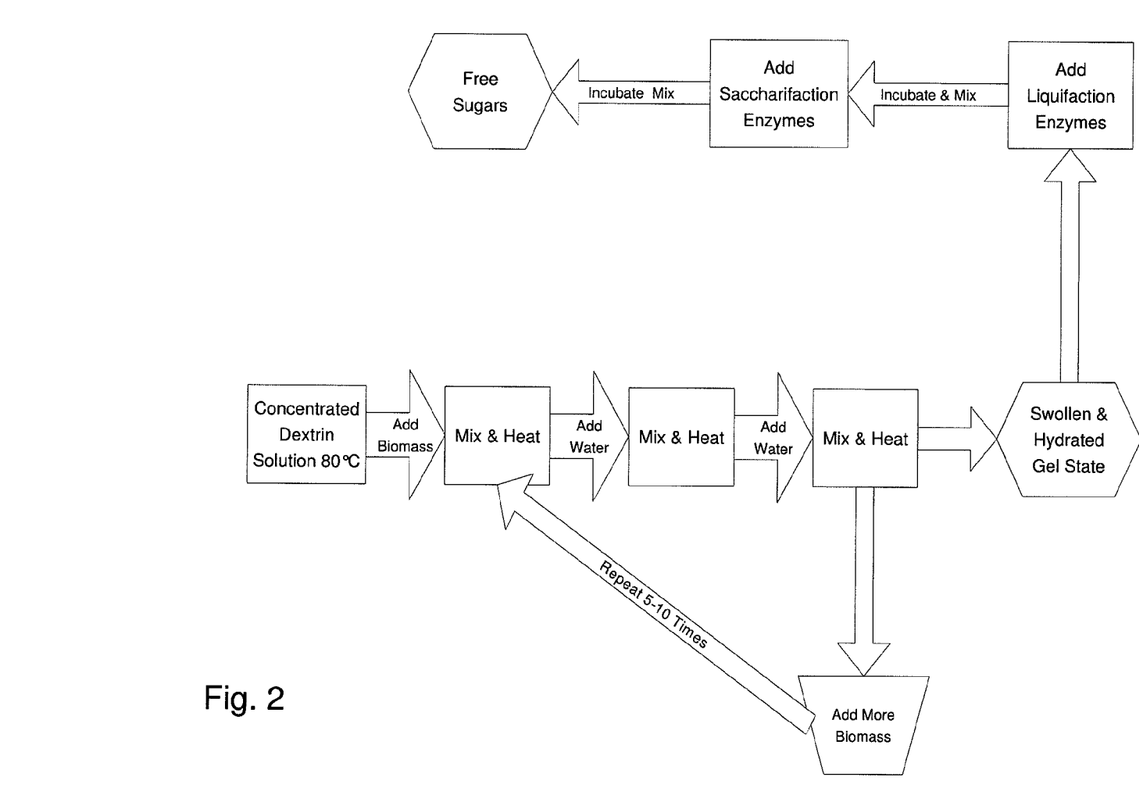
FIG. 2 is a flow diagram illustrating the use of dextrin to process cellulosic biomass.

The mixing-kneading (including the "beating" shear forces) has the mechanical effect of reducing the biological material (plant cell walls) to fibrils and sub-fibrils. At the same time the heat and the co-solvent help break down the paracrystalline regions of cellulose into soluble regions. The remaining fibrils swell and fall apart during this process—eventually becoming completely absorbed into the gel-solution. Depending on how the mixing-kneading and "beating" shear forces are applied, the process speed can be increased but the exact mechanical configuration of the processing equipment is not critical. The periodic addition of water (see FIG. 2) helps decrease excessive viscosity thereby achieving the most rapid swelling and hydration. Surprisingly, the presence of lignin in natural biomass appears to aid in this process. If the lignin is removed chemically as in making paper, the cellulose molecules are more resistant to the swelling and hydration. This implies that the cellulose structure becomes more rigid or resistant to solvation upon delignification.

When swelling and hydration was complete, the temperature was lowered to 60° C. (or lower—see above) and liquefaction enzymes were added to form an about 0.02% by weight enzyme solution. The gel became fully liquefied within about 30 min of additional mixing. The temperature was then lowered to about 50° C. and saccharification enzymes were added to make an about 0.05% by weight enzyme solution and the pH was adjusted to pH 4.5. The weight ratio of enzyme to biomass was about 1:100. After 3 hr of continued mixing, conversion of cellulose to glucose was at least 80% complete—some further hydrolysis was obtained with longer incubation. If the proper enzymes are included, the hemicelluloses will also be hydrolyzed to their constituent sugars. It will be appreciated that lower amounts of enzyme can be effective but result in longer processing times. Times, temperatures and pH should be varied depending on the precise enzymes employed.

Filter paper, Japanese cypress (*Cryptomeria*) softwood chips (2 mm), corn stover, bagasse, sweet sorghum straw, rice straw, rice husk and oil palm waste (EFB or empty fruit bunches of palm) have all been tested with the present dextrin process. All of these biomass materials can be dissolved by the present co-solvent method. It is believed that the method will work on essentially any cellulosic biomass. Table 1 shows the results with a number of different cellulosic particles (20-70 micrometer diameter produced as detailed above). A given weight of powder was added to a given weight of 82% dextrin solution and mixed/kneaded as described above. One or more additions of water were made as described above. The additions of water were necessitated by the viscosity during kneading. Easily solvated materials were less viscous and required less (or no) addition of water.

TABLE 1

| Raw Material | Dextrin | Addition 1 | Addition 2 | Addition 3 |
|---|---|---|---|---|
| EFB 50 g | 50 g | — | — | — |
| Corn Stover 50 g | 90 g | 11.87 g | 9.05 g | — |
| Rice Husks 50.61 g | 50.25 g | 4.54 g | 4.65 g | 6.80 g |
| Rice Straw 50.86 g | 72.05 g | 4.94 g | 6.05 g | 7.81 g |
| Sorghum Straw 50.55 g | 90.74 g | 5.62 g | 7.29 g | 7.61 g |

Following the kneading operation, each resulting gel-dough was hydrolyzed. First the material was diluted with 2 parts distilled water to 1 part kneaded biomass (by weight) and stirred (100-400 RPM) in a reaction vessel to produce a slurry. The pH of the material was adjusted to near neutrality (pH 6.5), and the material was heated to 60° C. for at least one hour to pasteurize it. Next the stirred biomass was allowed to cool to below about 50° C. and Meicellase at a weight ratio of 1:100 (enzyme to biomass) and a β-glucosidase rich enzyme (also at a weight ratio of 1:100) were added and the slurry was stirred for 24 hr. Note that liquefaction and saccharification occurred simultaneously. Samples were removed periodically and tested by HPLC. The results showed that hydrolysis was more than 50% complete at 6 hr. and 80% to near 100% complete at 20 hr. These results show that the degree of completion of hydrolysis is dependent on the starting material. Furthermore, the results show that the majority of hydrolysis occurs in the first hours and then slows thereafter.

The inventor believes that the rate and extent of enzymatic hydrolysis shown in the above experiments are an indication that the co-solvation of the cellulose is not complete. Cellulose that is co-solvated is rapidly hydrolyzed within the first hours. Then the remaining partially co-solvated cellulose is more slowly hydrolyzed. It is known in the art that the enzyme mixture used can achieve hydrolysis of untreated biomass if given enough time. As would be expected, the rate of such hydrolysis is dependent on the particle size of the biomass (surface/volume effect). For example, whole plant parts can take many days or longer to show significant enzymatic hydrolysis. Biomass material with maximum diameters in the 1-2 mm range show significant hydrolysis with a few days to one week. Material within the size range tested here (20-70 micrometers) generally shows significant hydrolysis in 2-3 days. Based on the results presented here, biomass that is totally co-solvated should show complete hydrolysis within a few hours at the most. It is clear, however, that the dextrin co-solvent-solvation process greatly accelerates the rate of cellulose hydrolysis.

The inventor believes that a drawback to the use of dextrin as a co-solvent is the necessity to use a very concentrated solution to provide sufficient viscosity to cause effective co-solvation upon kneading-mixing. This concentrated solution causes a gel having a high level of biomass to become more and more dough-like as solvation progresses. This requires increased temperature and addition of water to allow effective kneading. Even then if the dough is left unmixed and allowed to cool, it becomes an inflexible solid. Therefore, the inventor searched for a hydrophilic co-solvent that would produce adequate viscosity at a much lower concentration of co-solvent. With such a co-solvent the continued absorption of water by the biomass as it became hydrated and co-solvated would not result in hardening of the mixture. This would allow kneading to continue until essentially all the cellulose becomes hydrated and co-solvated. One possible such co-solvent is represented by dextrin with a higher DE number (as mentioned above). However, the inventor believes that hydrophilic polymers such as polyvinyl alcohol (PVA) provide an even more efficacious solution. The inventor has tested several types of PVA (as aqueous solution with concentrations of 5%, 10% and 20% by weight). The PVA tested was produced by the Kuraray Chemical Co., Ltd. (Osaka, Japan) and is sold as Poval 105, Poval 117, Poval 205 and Poval 217. The first numeral in the product name refers to either type 1 or type 2 PVA. Type 1 PVA has a hydrolysis level of 98-99% whereas Type 2 PVA has a hydrolysis level of only 87-89%. The second two numerals refer to the size of the polymer. The materials with "05" in their product names have mean polymerization numbers of 500 while the 117 products have polymerization numbers of 1700. The viscosity of the solution is affected by both the degree of hydrolysis and the degree of polymerization (polymerization number). As the degree of polymerization increases, a given weight percentage solution will be more viscous. However, as the hydrolysis level increases at a given polymerization number, the viscosity of the solution decreases.

An interesting property of PVA is that it can be crosslinked by a number of chemicals such as borates, titanium acetate, copper and other metal salts. The crosslinking occurs either by means of charge bridging with borates where the four negative charges of the borate ion are linked to positive charges on the PVA or the formation of a bridging metal binding site in the case of the metal salts. The ability to produce crosslinked PVA, which is a viscous, non-Newtonian fluid, allows one to use a hydrophilic polymer co-solvent with an initially high viscosity which does not become excessively thick and even solid during kneading as does biomass co-solvated with dextrin. When 5% by weight PVA solution is combined with a saturated solution of tetra-sodium borate (between 0.5 to 1 part of borate solution to 1 part of PVA solution), a workable "slime" is produced. This material remains relatively plastic when powdered biomass (20-70 micrometer diameter particles) is added and kneaded. The resulting mixture can be readily kneaded or mixed or even pressed repeatedly between rollers until the biomass material is completely hydrated and co-solvated.

Figure 3:
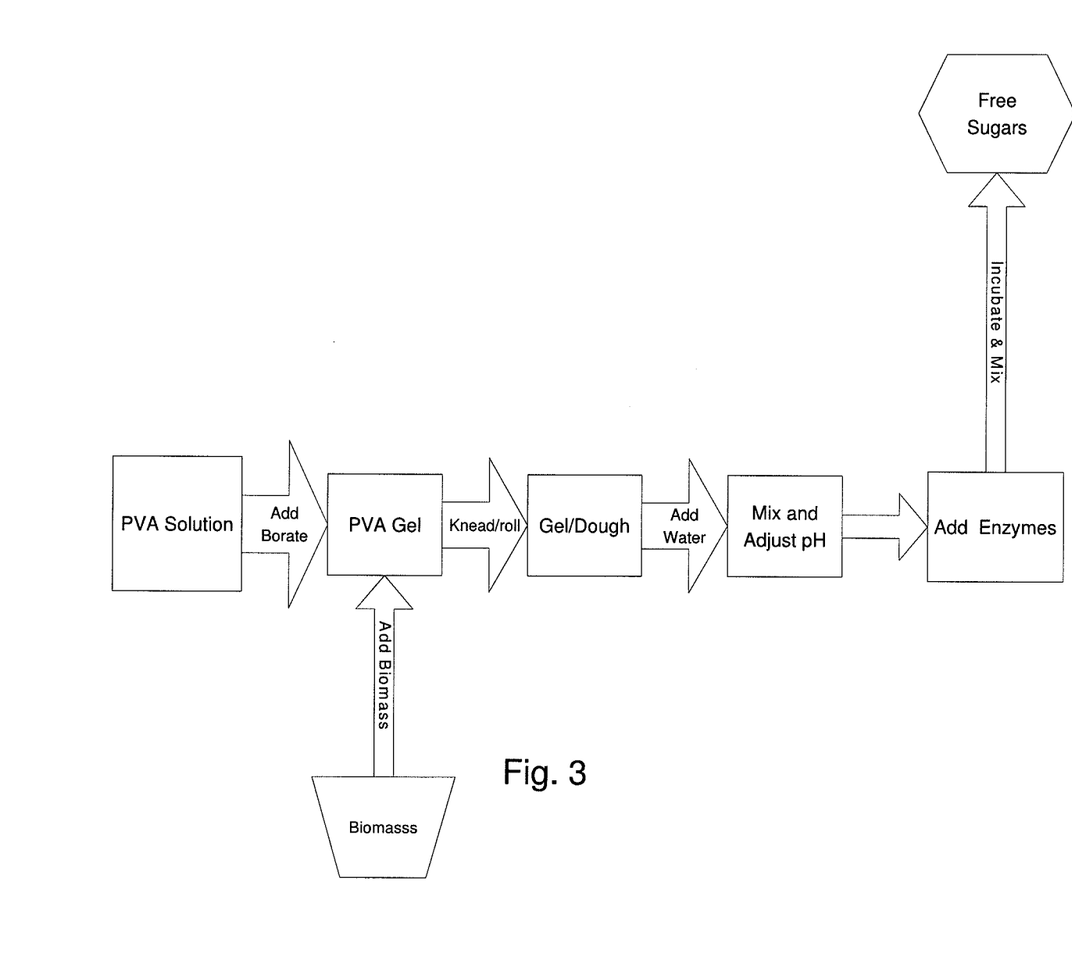
FIG. 3 is a flow diagram illustrating the use of PVA to process cellulosic biomass.
Figure 4:
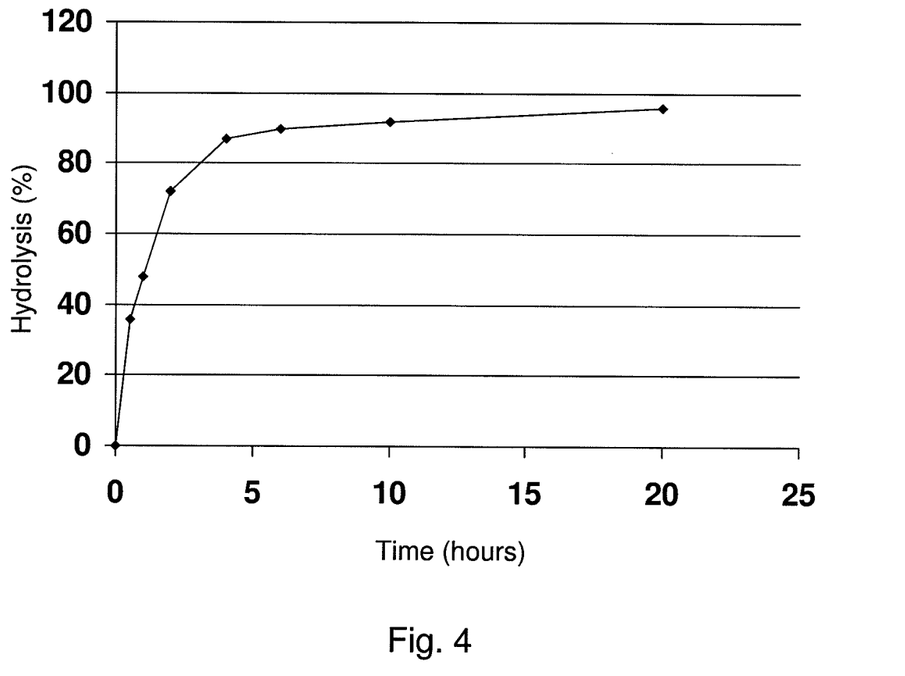
FIG. 4 is a graph showing the enzymatic hydrolysis of PVA processed cellulosic biomass.

The process using PVA slime is shown in FIG. 3. In a typical example a solution of 10% by weight PVA-205 was made with distilled water. The mixture was stirred and heated to about 70° C. to bring the PVA into solution. The resulting solution was only slightly more viscous than water. After the solution was cooled to room temperature 2 ml of a saturated aqueous solution of boric acid ($H_3BO_3$) was added and mixed. The resulting solution had a pH of 5.0. A small amount of a saturated aqueous solution of sodium borate (about 0.5 ml) was added and mixed. The resulting viscous slime had a pH of 6.5. EFB (palm oil empty fruit bunches) (20-70 micrometer diameter particles) was added to this gel and kneaded at room temperature. The resulting gel was relatively soft but as kneading continued, water (20 g-30 g) was lost as vapor and water was absorbed by the biomass so that the gel became more dough-like. The material could be easily rolled flat and stacked. The stacked material was folded to break the dough which was then gathered together and rolled again. Small aliquots of material were removed from time to time, diluted in water and examined microscopically. It was possible to observe particle size decreasing and the cellular structures breaking down as the processing progressed. The breakdown process was rapid in thick hard gel but largely absent from thin gel. This suggests that transmission of mechanical force is an essential part of the process. Adding a larger proportion of biomass powder increases the viscosity and accelerates the process. The optimal content of biomass solid seems to be around 40% by weight. Lower amounts of biomass tend to produce a material that is too thin to knead and roll efficiently. Higher amounts of biomass may produce a mass that is too viscous to work efficiently. Varying concentrations and types of PVA can also be used to modulate the viscosity. Under optimum conditions the kneading process is complete in about one hour. This is generally much faster than the dextrin processing which can take one hour for each cellulose addition After the kneading was complete (as judged microscopically), about 130 ml of distilled water was mixed into the resulting gel-dough to reduce its viscosity. A small amount of HCl was then added to adjust the pH to 6.0 since the hydrolytic enzymes prefer a somewhat acidic milieu. The resulting liquid was of medium viscosity similar to that of melted chocolate. Meicellase (Meiji Seika Co. Ltd.) and *Acremonium* cellulase (a commercial cellulase prepared from the fungus *Acremonium cellulolyticus* and obtained from Meiji Seika Co. Ltd.) were added at a weight ratio of enzyme to biomass of 1:100 for each enzyme mixture. The resulting mixture was stirred in a reaction vessel at a temperature of 50° C. Within minutes of enzyme addition, the viscosity of the mixture decreased noticeably. FIG. 4 is a time course graph illustrating the hydrolysis of the biomass over time. The Percent Hydrolysis was obtained by comparing the actually measured quantity of reducing sugars with the theoretical amount of such sugars available in the biomass from the hydrolysis of polysaccharides. The advantage of this approach to one where determination of the degree of hydrolysis is strictly weight based is that it automatically eliminates non-hydrolysable components (e.g., mineral inclusions, cuticle, lignin, etc.) from consideration. The drawback is that the 100% figure is based on a theoretical quantity, and it is somewhat unlikely that actual biomass samples will contain precisely the calculated amount of hydrolyzable polysaccharides. The graph shows that hydrolysis proceeded rapidly and was largely complete after 4 hours. At 4 hours calculated hydrolysis was 87% whereas 16 hours later the percent of hydrolysis had increased only an additional 9% to 96% completion. It seems likely that the 9% improvement was due to slower hydrolysis of particles that had not been completely broken down by the PVA conditioning treatment. If that is true, longer kneading would decrease the overall hydrolysis time. It is currently not known if any hydrolyzable polysaccharide remains at 20 hours because of the error inherent in the calculation method. The residue will be analyzed to discover the true level of residual carbohydrate.

In any case, it is herein demonstrated that nearly total hydrolysis can be achieved within a few hours. The PVA process achieves faster conditioning/break down of biomass as compared to the dextrin process—and the optimum process takes place at room temperature. Even though the processing is more rapid, the hydrolysis is also more complete. The optimum combination of processing time and enzyme amount vs. hydrolysis time has probably not yet been accomplished. One of skill in the art will appreciate that the fastest, lowest cost process is the goal. Decreasing the particle size of the initial biomass results in a speed increase in the conditioning/kneading process. However, decreasing the particle size requires time and energy. Increasing the conditioning/kneading time reduces the hydrolysis time and required enzyme amount, but conditioning kneading beyond the point of breakdown of cellular structures is of little or no benefit. Once optimum conditioning/kneading is achieved, the amount of enzyme can be reduced by increasing the hydrolysis time. In a real world scaled-up process these various factors will be adjusted and selected to minimize costs (time, energy, labor and material costs).

Figure 5:
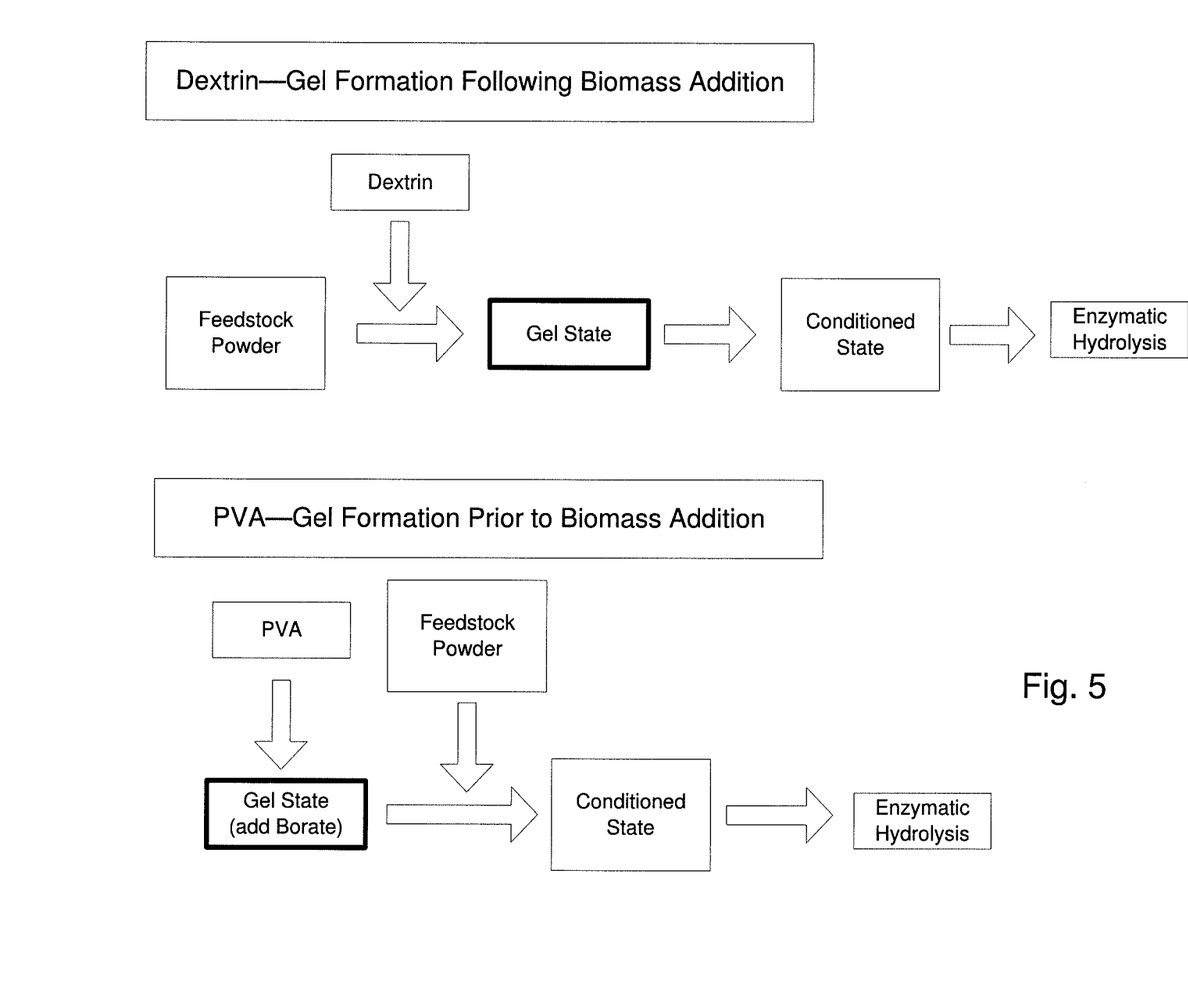
FIG. 5 is a flow diagram contrasting the gel formation in the dextrin versus the PVA process.

Conceptually the dextrin process differs from the PVA process in that with dextrin although the starting dextrin solution is fairly viscous, it is not gel-like. With the dextrin process the dextrin and the biomass are mixed at an elevated temperature and a gel is formed. It is believed that the presence of a gel greatly enhances the ability of mechanical mixing (kneading) to disrupt the cellulose. With the PVA process the PVA solution is first crosslinked by the addition of borate to form a gel. Then the biomass is mixed into this gel. Because the gel is preformed, the conditioning action is much more rapid and effective. The differences between the processes are illustrated diagrammatically in FIG. 5.

Figure 6:
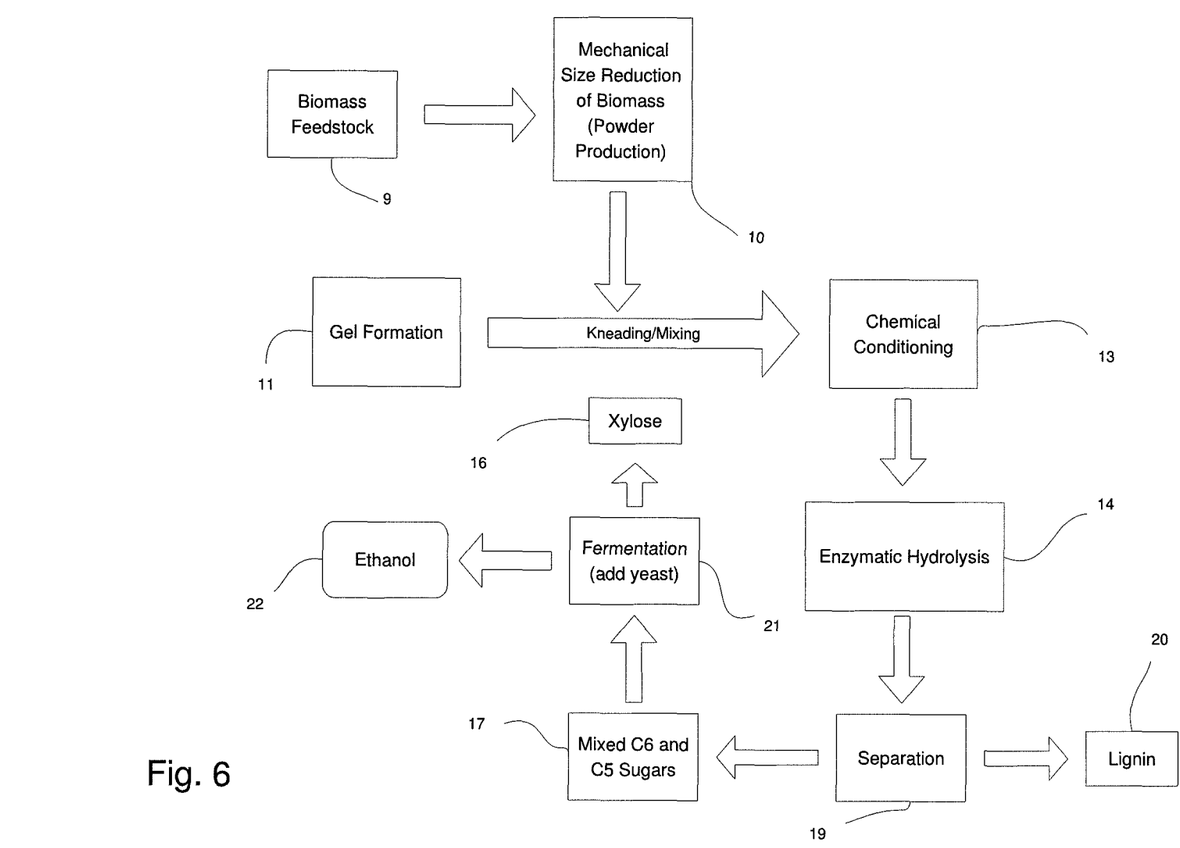
FIG. 6 is a flow diagram of the overall process using PVA.

FIG. 6 shows a version of FIG. 1 updated to show the layout for the PVA process. First the biomass feedstock 9 is reduced to an optimum particle size (powder) (step 10). Note that with PVA the gel formation and conditioning steps are separate. In step 11the PVA gel is formed by crosslinking the PVA. In step 13 the biomass powder is added to the PVA gel and mixing-kneading ensues to hydrate the cellulose and break down the cell structures. Following conditioning water is added at step 15 to reduce viscosity. Enzymes 14' are mixed in and hydrolysis takes place in step 14. In step 19 the lignin 20 is separated from the mixed C5 and C6 sugars 17. The addition of yeast starts fermentation 21 which produced ethanol 20 (which is separated from the mixture by distillation leaving xylose 16 which can be reclaimed from the yeast mixture. Alternatively, xylose can be separated from the mixed sugars 17 by, for example, chromatograph. Both ethanol and xylose are valuable products. Lignin can also be viewed as either a product to be sold for chemical uses or lignin can be burned to directly release energy.

The following claims are thus to be understood to include what is specifically illustrated and described above, what is conceptually equivalent, what can be obviously substituted and also what incorporates the essential novel features of the invention. Those skilled in the art will appreciate that various adaptations and modifications of the just-described embodiments can be configured without departing from the scope of the invention. The illustrated embodiments have been set forth only for the purposes of example and that should not be taken as limiting the invention. Therefore, it is to be understood that, within the scope of the appended claims, the invention may be practiced other than as specifically described herein.

What is claimed is:

1. A process for converting cellulosic biomass into a readily hydrolyzable mixture comprising the steps of:
   forming a polyvinyl alcohol gel by crosslinking an aqueous solution of polyvinyl alcohol;
   combining cellulosic biomass particles with the crosslinked polyvinyl alcohol gel to form a gel-biomass mixture; and
   mixing-kneading the gel-biomass mixture to convert the gel-biomass mixture into swelled and hydrated biomass in a gel-like state wherein the cellulose is amenable to enzymatic hydrolysis.

2. The process of claim 1, wherein the polyvinyl alcohol gel is formed by adding borate ions to the aqueous solution of polyvinyl alcohol.

3. The process of claim 1, wherein the biomass particles have average diameters of less than about 100 micrometers.

4. The process of claim 3, wherein the biomass particles have average diameters of about 20-70 micrometers.

5. The process according to claim 1 where liquefaction and saccharification enzymes are added to the swelled and hydrated biomass to liquefy and hydrolyze it into free sugars.

6. The process of claim 1, further comprising a step of heating the gel-biomass mixture to at least about 70° C. during the step of mixing-kneading.

7. The process of claim 1 wherein the biomass particles constitute about 40% by weight of the gel-biomass mixture.

8. The process according to claim 1 further comprising a step of periodically adding water to reduce the viscosity of the gel-biomass mixture.

9. The process according to claim 1 further comprising a step of periodically adding additional biomass particles to the gel-biomass mixture.

\* \* \* \* \*